US00PP37371P3

(12) United States Plant Patent
Hansen

(10) Patent No.: US PP37,371 P3
(45) Date of Patent: Apr. 14, 2026

(54) ***HOSTA* PLANT NAMED 'Time's Up'**

(50) Latin Name: ***Hosta* hybrid (Tratt.)**
Varietal Denomination: Time's Up

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 293 days.

(21) Appl. No.: 18/831,119

(22) Filed: Jul. 25, 2024

(65) Prior Publication Data

US 2026/0033415 P1 Jan. 29, 2026

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./263.1, 353
See application file for complete search history.

(56) References Cited

U.S. PATENT DOCUMENTS

PP18,318 P2 * 12/2007 Bergeron ..... A01H 6/12 Plt./353
PP33,267 P2 * 7/2021 Hansen ..... Plt./353

* cited by examiner

*Primary Examiner* — Karen M Redden

(57) ABSTRACT

A new and distinct *Hosta* plant named 'Time's Up' of arching, lanceolate, variegated leaves having a lustrous underside and moderately wavy margins. The foliage has dark green margins and yellowish-chartreuse centers. 'Time's Up' has excellent, small, compact, mounded habit and is useful in the landscape, in containers, as a specimen, or en masse.

1 Drawing Sheet

Botanical classification: *Hosta* hybrid (Tratt.).
Variety denomination: 'Time's Up'.

STATEMENT REGARDING PRIOR DISCLOSURES UNDER 37 CFR 1.77(b)(6)

No plants of *Hosta* 'Time's Up' have been sold, in this country or anywhere in the world, nor has any disclosure of the new plant been made, more than one year prior the filing date of this application.

BACKGROUND AND ORIGIN OF THE PLANT

The present invention relates to a new and distinct *Hosta* plant, *Hosta* 'Time's Up' hereinafter also referred to as the new plant or by the cultivar name, 'Time's Up'. *Hosta* 'Time's Up' was discovered on May 1, 2024, by the inventor as a whole plant mutation of 'Time in a Bottle' U.S. Plant Pat. No. 33,267 at a wholesale perennial nursery in Zeeland, Michigan, USA. The new plant was assigned the breeder code 24-SP-HOST-1331 and passed the initial evaluation in the spring of 2024. It has been asexually propagated by division at the same nursery since 2024 with the resultant asexually propagated plants having retained all the same traits as the original plant.

There are over 7,000 registered and unregistered *Hostas* with The American *Hosta*Society, which is the International Cultivar Registration Authority for the genus *Hosta*. Some of these have chartreuse leaf blades with wavy margins. The most similar *Hosta* cultivars known to the applicant are 'First Mate' (not patented), 'Imp' (not patented), 'Kabitan' (not patented); 'Sea Sprite' (not patented), and 'Pineapple Upsidedown Cake' (not patented).

'First Mate' has wider dark green margins and flatter less sinuate leaves without the reddish spotting on the petiole. 'Kabitan' has similar variegation, but the foliage is more arching, and the petioles lack reddish spotting. 'Sea Sprite' has slightly broader foliage and the center is a lighter yellowish-chartreuse. 'Pineapple Upsidedown Cake' is larger in habit and foliage size, the leaf blades are slightly wider, and the leaf center is lighter yellowish-chartreuse.

The parent has foliage that is solid chartreuse without the green margin.

Other *Hosta* cultivars may have traits similar to 'Time's Up' but the new plant differs from the above listed cultivars and all other *Hostas* known to the applicant, by the combination of the following traits.

1. Leaves are small-sized, lanceolate, with narrowly acute apices and attenuate base;
2. Arching leaves have a moderately wavy margin;
3. Variegated leaves have yellowish-chartreuse centers and dark green margins;
4. Underside of leaf lustrous;
5. The petiole develops a strong reddish spotting;
6. Compact mounded habit and useful in the garden as edging or front border, in containers, as a specimen or en masse.

BRIEF DESCRIPTION OF THE DRAWING

The photograph of the new plant demonstrates the overall appearance of a one-year-old plant, including the unique traits. The colors are as accurate as reasonably possible with color reproductions. Ambient light spectrum, temperature, source, and direction may cause the appearance of minor variation in color.

The drawings show the new plant in a contain grown in a partially shaded display garden at a nursery in Zeeland, MI with supplement fertilizer and water as needed.

DETAILED BOTANICAL DESCRIPTION

Figure 1:
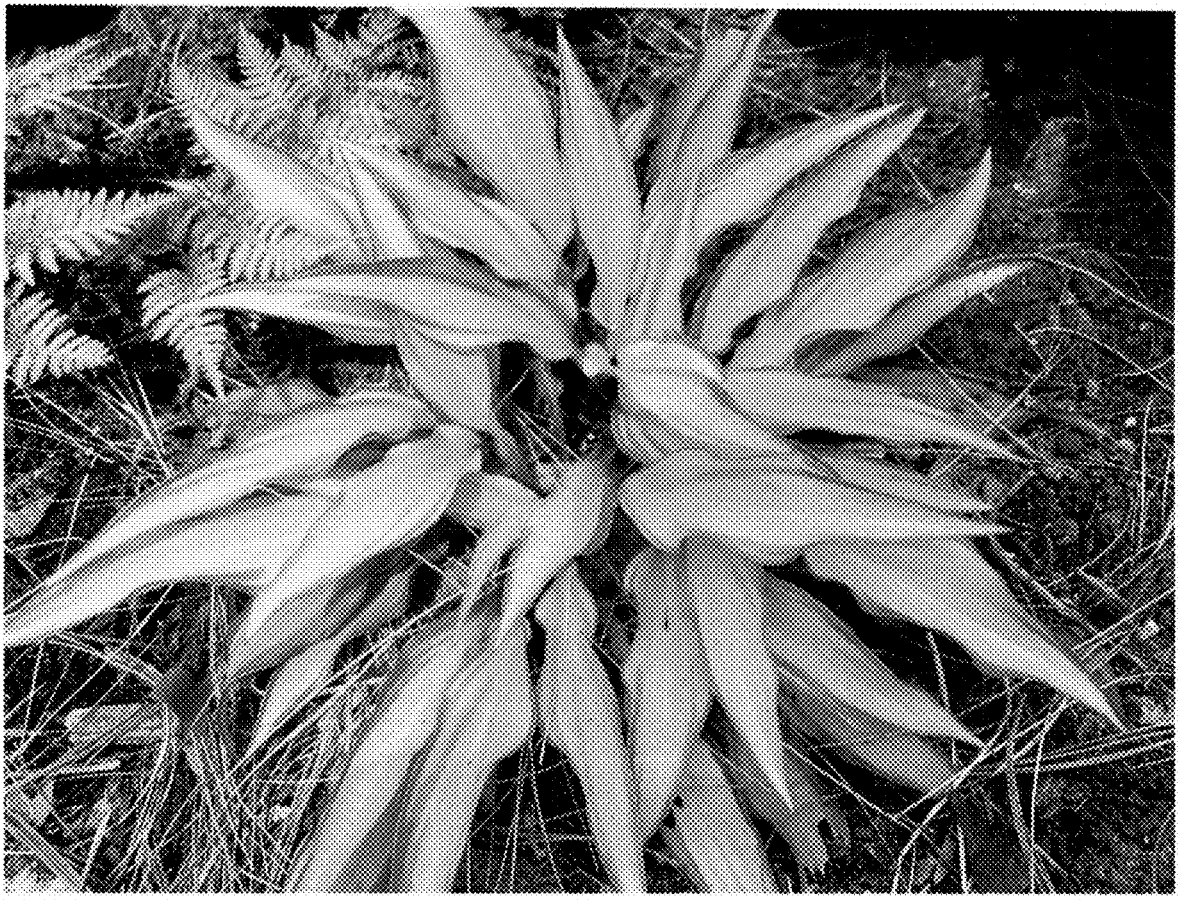
FIG. 1 shows a view of the plant from above.
Figure 2:
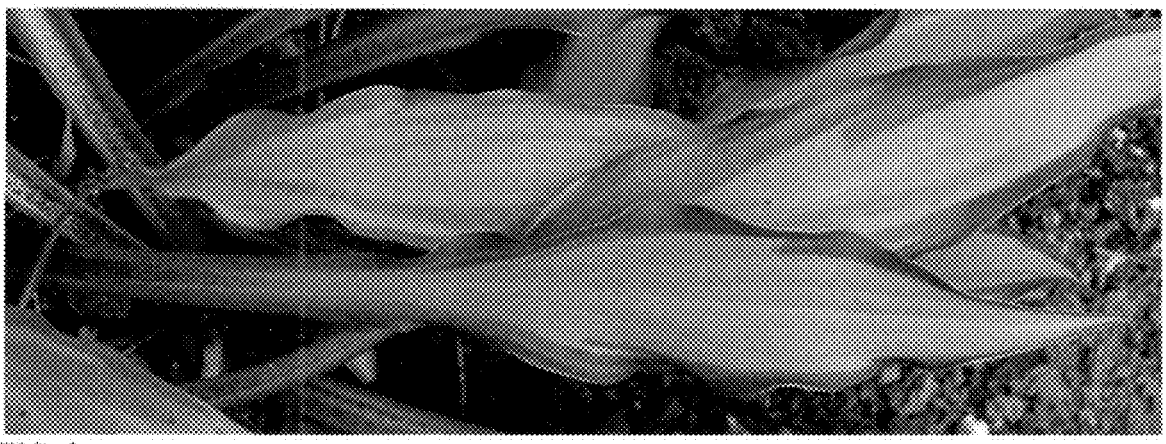
FIG. 2 shows a close-up of the foliage with reddish spotting on petiole.

The following descriptions and color references are based on the 2015 edition of The Royal Horticultural Society Colour Chart except where common dictionary terms are used. The new plant, *Hosta* 'Time's Up', has not been observed under all possible environments. Those skilled in the art will appreciate that certain characteristics will vary with plants that are more mature or plants that are less mature. The phenotype may vary slightly with different environmental conditions, such as temperature, light, fertility, moisture, and maturity levels, but without any change in the genotype. The following observations and size descriptions are of a one-year-old plant in a shaded trial garden in Zeeland, Michigan with supplemental water and fertilizer:

Botanical classification: *Hosta* x hybrid;

Parentage: Whole plant mutation of 'Time in a Bottle';

Propagation: Garden division;

Time to initiate roots from tissue culture: About two weeks;

Growth rate: Moderately vigorous;

Crop time: About three months to four months to finish during the spring in a one-liter container from rooted tissue culture plantlet;

Rooting habit: Fleshy, lightly branching;

Root color: Nearest RHS NN155C when actively growing;

Plant shape and habit: Hardy herbaceous perennial with basal rosette of leaves emerging from rhizomes producing a short, compact, mound of arching petioles and leaves; with five divisions having about 6 to 8 leaves per division;

Plant size: Foliage height about 17 cm above soil line to the top of the leaves and about 38 cm wide at the widest point at the soil line;

Foliage description: Lanceolate; narrowly acute apex, attenuate base; margin entire, moderately sinuate; flexible; smooth, without blistering, dimpling or bulging; glabrous and dull adaxial and glabrous and slightly lustrous abaxial;

Leaf blade size: To about 13 cm long and 3 cm wide; average about 12 cm long and 2.5 cm wide; margin to about 4 mm wide above and 3 mm wide below;

Leaf blade color: Young adaxial center between RHS N144A and RHS N144D, adaxial margin abaxial nearest RHS 144A, with random striations between center and margin of nearest RHS N144D; young abaxial center nearest RHS N144D, and abaxial margin nearest RHS 143A, with random striations of nearest RHS 145A; mid-season and later adaxial center between RHS 146D and RHS 145A, adaxial margin between RHS 139A and RHS 137A, with region between center and margin of mid-season between RHS 146C and RHS 146B; midseason and later abaxial center nearest RHS 146D, margin between RHS 139A and RHS 137A, with region between center and margin between RHS 144A and RHS 146B;

Petiole: Glabrous adaxial and abaxial; dull adaxial, slightly lustrous abaxial; shallowly concavo-convex; flexible; to 6 cm long, 9 mm wide at base and 3 mm deep; average about 5.5 cm long and 8 mm wide; maculate with spots on adaxial and abaxial between 0.2 mm and 1 mm diameter;

Petiole color: Young adaxial and abaxial center between RHS N144A and RHS N144D and heavily maculate with spots nearest RHS 183C, young adaxial and abaxial margin between RHS N144D and RHS 144C sparsely maculate with spots nearest RHS 183C; mature adaxial and abaxial center nearest RHS 145A and densely maculate and more concentrated proximally and less concentrated distally with nearest RHS 183A, mature adaxial and abaxial margin between RHS 137A and RHS 139A sparsely maculate with spots nearest RHS 183A, mature adaxial and abaxial intermediate region between center and margin between RHS 145A and RHS 146D, proximal one-half densely maculate with nearest RHS 183A and distal one-half moderately to sparsely maculate nearest RHS 183A;

Veins: Typically, up to five pairs and midrib; parallel; glabrous adaxial and abaxial; smooth on adaxial and slightly costate abaxial;

Veins color: Adaxial center nearest and between RHS 146D and RHS 151D and margin nearest RHS 137A, abaxial center between RHS 146D and RHS N144D and margin nearest RHS 137A;

Flower description—

Buds one to two days prior to maturity: Elongated ovoid; acute apex; base cordate to reflexed around distal 1 mm of pedicel; about 45 mm long and 8 mm in diameter near the middle; no restricted tube or tapered portion;

Bud color: Between RHS 85A and RHS N87D;

Inflorescence: Cylindrical; glabrous; slightly lustrous; to about 59 cm long and 3 mm diameter at base; aspect leaning at about a 45-degree angle; with about 24 flowers in the terminal 27 cm; to about 7 cm wide; flowers distinctly secund;

Flowers: Perfect; single; incomplete; remaining closed through dehiscence; aspect mostly horizontal, slightly downwardly; to 30 mm long, 9 mm diameter near middle, tapering to 4 mm diameter at base;

Flower lasting: Persists for about three days following maturity; scapes remain effective with flowers beginning late July to early August for about four weeks; with about 44 flowers per scape; no detectable fragrance;

Flowering period: Scapes remain effective with flowers beginning mid-August for about three weeks; with about 24 flowers per scape;

Flower fragrance: None detected;

Tepals: Two nearly identical sets of three, glabrous; lanceolate; entire margins; narrowly acute apices, about 30 mm long and fused in the basal 13 mm;

*Inner set*.—Approximately 6 mm wide slightly above fusion point.

*Inner set color*.—Adaxial nearest RHS 79C; abaxial outer edge nearest RHS N82D, central portion including tube nearest RHS 83D.

*Outer set*.—Approximately 6 mm wide slightly above fusion point.

*Outer set color*.—Adaxial nearest RHS 79C; abaxial between RHS 83D and RHS 83C.

Gynoecium: One to seven per flower; to 24 mm long; superior;

*Style*.—One larger central style surrounded by up to 6 thinner styles; cylindrical; thinner outer styles twisted and distortedly bent; variable; inner style to about 15 mm long and 1 mm diameter, outer styles to about 26 mm long and 0.5 mm diameter; color nearest RHS 145D.

*Stigma*.—Puberulent; rounded; variable; about 1 mm to 0.5 mm across and 0.5 mm tall; color nearest RHS NN155A.

*Ovary*.—Ovoidal; superior; apex truncate; base truncate; to about 4 mm long and 3.5 mm diameter in middle; color apex and base nearest RHS N79A, with longitudinal lines of nearest RHS 145B.

Androecium: Not observed;

*Filaments*.—Not observed.

*Anthers*.—Not observed.

*Pollen*.—Not observed.

Peduncle: Cylindrical; usually one per mature division; about 4 per plant; glabrous; moderately glaucous; arching to leaning with maturity; to about 52 cm tall, and about 3 mm in diameter at base, average about 48 cm tall and 3 mm diameter at base;

Peduncle color: Between RHS 147B and RHS 147C heavily maculate with nearest RHS 183B;

Pedicel: Cylindrical; glabrous; slightly lustrous; curved slightly downward; to about 15 mm long and 1 mm diameter, decreasing in length distally;

Pedicel color: Nearest RHS 147C with a moderate blush nearest and RHS 86B;

Floral bracts: Each flower normally subtended by a single bract; lanceolate; narrowly acute apex and truncate clasping base; entire margin; strongly concavo-convex; glabrous and slightly glaucous abaxial and adaxial; to about 15 mm long 4 mm wide, decreasing distally;

Proximal bract: One or two proximal bracts on nodes below first flower, to about 75 mm long and 13 mm across; ovate; with acute apex and cuneate base; color adaxial and abaxial margin nearest RHS 138A with blush of nearest RHS 183A, color adaxial and abaxial center nearest RHS N144D with narrow veins blushed nearest RHS 183A;

Floral bract color: Proximal bracts at time of flowering adaxial and abaxial longitudinal center between RHS 145D and RHS N144D with a blush of nearest RHS 183A, adaxial and abaxial margins nearest RHS 86C;

Fruit: Not observed;

Seeds: Not observed;

Disease resistance: Resistance to pests (including: *Odocoileus virginianus* and *Oryctotagus cuniculus*) and diseases common to *Hostas* is equal that typical of other cultivars. The plant grows best and shows the best coloration with plenty of moisture, adequate drainage, and light shade, but is able to tolerate some drought when mature.

Hardiness at least from USDA zone 3 through 8, and other disease resistance is typical of that of other *Hostas*.

It is claimed:

1. A new and distinct *Hosta* plant cultivar named *Hosta* 'Time's Up' as herein described and illustrated.

* * * * *